Oct. 26, 1954 E. S. BOERNER Plant Pat. 1,310
CHRYSANTHEMUM PLANT
Filed Nov. 13, 1953
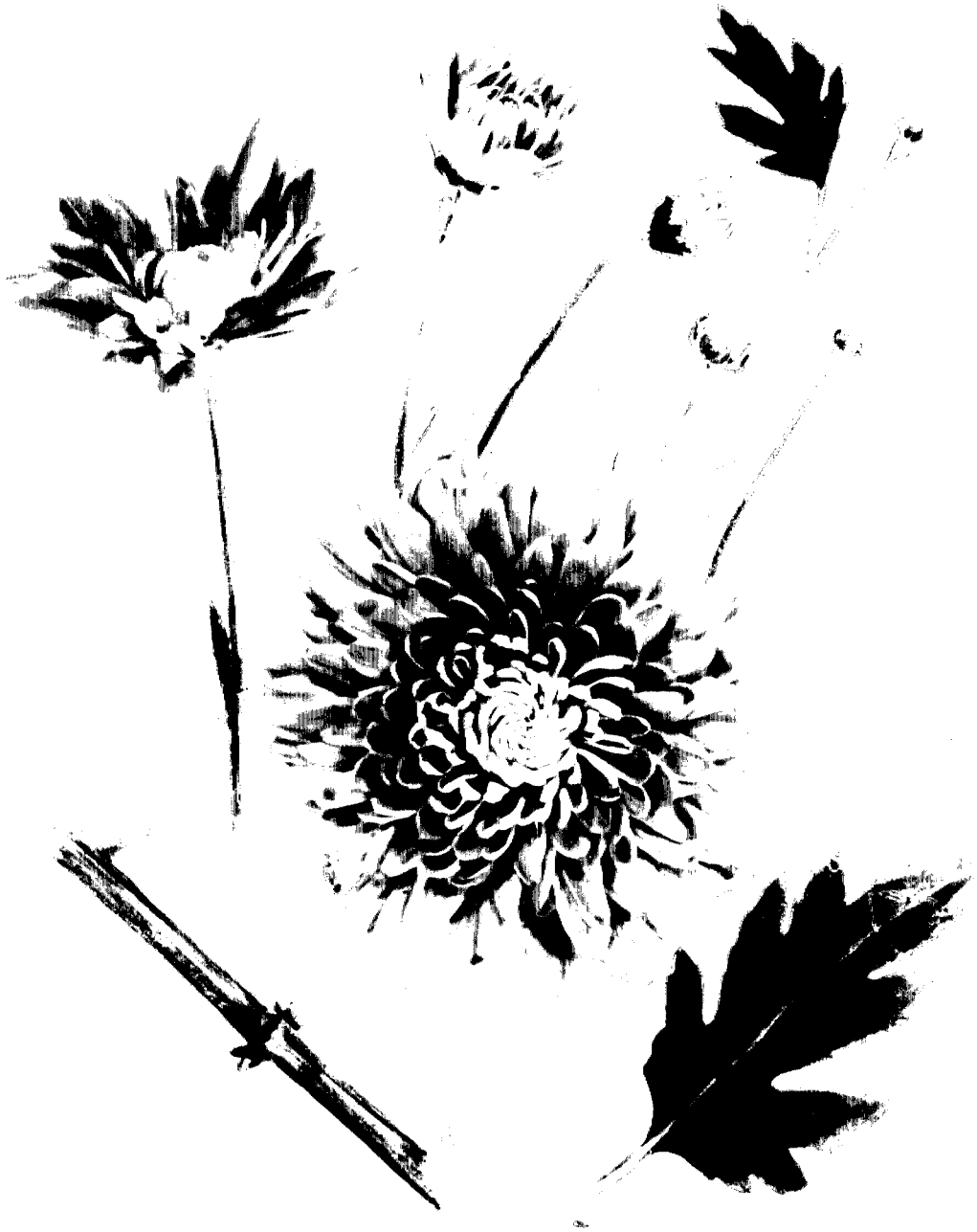
Inventor.
E. S. Boerner
By: Cobb & Cobb
Attorneys.

Patented Oct. 26, 1954

Plant Pat. 1,310

UNITED STATES PATENT OFFICE 1,310

CHRYSANTHEMUM PLANT

Eugene S. Boerner, Newark, N. Y., assignor to Jackson & Perkins Company, Newark, N. Y., a corporation of New York Application November 13, 1953, Serial No. 392,074

1 Claim. (Cl. 47—60)

The present invention relates to a new and distinct variety of chrysanthemum plant which was originated by me by crossing the variety "September Dawn" (unpatented) with an unnamed and unpatented large-flowered seedling identified in my breeding records as "L-6."

The primary objective in making this cross was to produce a new variety of chrysanthemum plant which bears larger flowers, but which retains the floriferousness and the early blooming habit of the parent variety "September Dawn." This objective was fully achieved, together with the attainment of a new color combination in the flowers of my new variety.

My new variety is distinguished from its parents, as well as from all other varieties of its class, by the following unique combination of dominant characteristics which represent the most outstanding features of the new variety:

(1) General characteristics of the plant similar to "September Dawn";

(2) Larger flowers than those of either parent, but blooming begins earlier than is the case of the seedling parent "L-6";

(3) The distinctive shape, large size and sweet fragrance of the flowers, the latter being quite different from the ordinary chrysanthemum fragrance; and (4) The distinctive color of the flowers which may be specifically characterized as Spinel Red in general color tonality.

Asexual reproduction of my new variety by top cuttings and also by underground runners at Newark, New York, shows that the foregoing characteristics and distinctions come true to form and are established and transmitted through succeeding propagations.

The accompanying drawing shows typical specimens of the flowers, foliage and stems of my new variety in different stages of development and depicted in color as nearly true as it is reasonably possible to make the same in a color illustration of this character.

The following is a detailed description of my new variety as based upon observations made in a field at Newark, New York in the early morning and in the early part of the month of October, with color terminology in accordance with Ridgway's Color Standards and Nomenclature:

Parentage: "September Dawn" × a large-flowered seedling identified as "L-6."

Classification: Semi-incurved.

Growth: Approximately 3 feet tall.

Cold resistance: Plants are very winter hardy in northern New York; flowers are frost resistant, as determined from comparison with other varieties grown under comparable cultural conditions at Newark, New York.

Blooming habit: In Newark, New York, climatic area, blooming starts about October 1st and continues until heavy frost.

Bud:

*Color.*—When sepals first divide — Spinel Pink, Plate 26, lightly overcast with Barium Yellow, Plate 16. When petals begin to unfurl — Spinel Red, Plate 26. When half blown: inside of petals—Spinel Red, Plate 26, lightly overcast with Rose Color, Plate 12; Reverse of petals—Deep Rose Pink, Plate 12, lightly overcast with Light Orange-Yellow, Plate 3.

*Peduncle.*—Color—Light Cress Green, Plate 31. Strength—strong.

Bloom:

*Size.*—From 4½ to 5 inches.

*Stems.*—Stiff; long.

*Form.*—Semi-incurved.

*Petalage.*—Double.

*Color.*—Center of flower—Indian Lake, Plate 26. Outer petals—Rose Color, Plate 12, lightly overcast with Spinel Red, Plate 26. Base of petals—Light Lumiere Green, Plate 17. Inside of petals—Spinel Red, Plate 26. Reverse of petals—Cartridge Buff, Plate 30, lightly overcast with Thulite Pink, Plate 26.

*Petals.*—Texture—stiff. Form—flat.

*Fragrance.* — Sweet chrysanthemum fragrance.

Plant:

*Form.*—Compact; bushy.

*Growth.*—Free.

Foliage:

*Size.*—Medium-large

*Quantity.*—Abundant.

*Color.*—Upper side—Bice Green, Plate 17. Reverse side—Light Bice Green, Plate 17.

*Texture.*—Leathery.

I claim:

A new and distinct variety of chrysanthemum plant of the semi-incurved type, substantially as herein shown and described, characterized particularly as to novelty by the similarity of its plant characteristics and floriferousness to those of the parent variety "September Dawn" (unpatented), by its early blooming habit, by the distinctive shape, large size and sweet fragrance of its flowers, and by the distinctive Spinel Red general color tonality of its flowers.

No references cited.